United States Patent
Arquette

(10) Patent No.: US 7,029,709 B2
(45) Date of Patent: *Apr. 18, 2006

(54) COMPOSITION AND METHOD TO WHITEN AND EXFOLIATE SKIN

(75) Inventor: James Demetrios G. Arquette, Tempe, AZ (US)

(73) Assignee: Desert Whale Jojoba Company, Tucson, AZ (US)

(*) Notice: Subject to any disclaimer, the term of this patent is extended or adjusted under 35 U.S.C. 154(b) by 162 days.

This patent is subject to a terminal disclaimer.

(21) Appl. No.: 10/342,497

(22) Filed: Jan. 15, 2003

(65) Prior Publication Data

US 2004/0052740 A1    Mar. 18, 2004

Related U.S. Application Data

(63) Continuation-in-part of application No. 10/236,362, filed on Sep. 6, 2002.

(51) Int. Cl.
*A61K 35/78* (2006.01)

(52) U.S. Cl. .................................................... 424/725
(58) Field of Classification Search ................ 424/725, 424/195.1
See application file for complete search history.

(56) References Cited

U.S. PATENT DOCUMENTS

2003/0008022 A1* 1/2003 Mogy ......................... 424/757

* cited by examiner

*Primary Examiner*—Patricia Leith
(74) *Attorney, Agent, or Firm*—Dale F. Regelman

(57) ABSTRACT

A composition which is effective as a skin whitening and skin exfoliation agent. The composition includes one or more hydroxy acids in combination with one or more extracts of one or more jojoba plant parts. The composition further includes Simmondsin. A method of promoting skin whitening and skin exfoliation, comprising the step of topically administering to an individual a composition in an amount effective to whiten and exfoliate skin, where that composition comprises one or more hydroxy acids in combination with one or more jojoba extracts.

12 Claims, 2 Drawing Sheets

COMPOSITION AND METHOD TO WHITEN AND EXFOLIATE SKIN

RELATED APPLICATIONS

This is a Continuation In Part of pending application having Ser. No. 10/236,362 filed on Sep. 6, 2002, and assigned to the common assignee hereof.

FIELD OF THE INVENTION

Applicant's invention relates to a composition and method to whiten and exfoliate skin.

BACKGROUND OF THE INVENTION

Exposure to the sun over time can induce many biochemical reactions in the skin. For example, exposure can lead to sunburn and tanning, which are immediate and well recognized. Other consequences of exposure to the sun are more subtle and accumulate over time. Often melanocytes can accumulate and the action of the enzyme tyrosinase is increased. These changes can result in the development of age spots and create an uneven, mottled skin tone. Unfortunately, many of the commercially available products in today's market are either only marginally effective, or contain active agents that are unstable and lose their potency when incorporated into a final formula.

The ability to modify the expression of pigment content in the skin, to promote an even-looking skin tone and a more youthful appearance, is highly desired in today's society. Many people desire to modify their skin tone, to reduce aging spots, melasma, etc., or for purely cosmetic reasons. In fact, in the Far East, a lighter skin tone is desirable and is associated with higher socioeconomic status.

Hyper-pigmentation in the skin is caused by the over expression or accumulation of melanin in the skin. As a result, the pathway involved in melanin production has been the target for many inhibitors so as to reduce the levels produced. One of the principal enzymes involved in the melanin pathway is tyrosinase.

Skin functions include, inter alia, protection, heat regulation, immune response, and sensory detection. With age, the skin's natural rejuvenation process slows. In addition, skin aging many times results in development of not only hyperpigmentation, but also hyperkeratinization wherein corneocytes adhere in excess causing a thickening of the stratum corneum. The stratum corneum comprises a portion of the epidermis, and includes nonviable corneocytes which are cells that have lost the nucleus and cytoplasm organelles.

What is needed is a composition which can be effectively used as a topically applied skin whitening and skin exfoliation agent. More particularly, it is desirable to have a topical composition which can whiten skin as well as induce shedding of dry scales from the skin's surface thereby promoting a rejuvenated, fresher complexion. Applicant has now discovered a composition comprising tyrosinase inhibitors, and/or melanin cell synthesis inhibitors, in combination with skin exfoliating agents, which is useful in topically applied cosmetic and pharmaceutical formulations.

SUMMARY OF THE INVENTION

Applicants' invention includes a composition which is effective as a skin whitening agent. Applicant's composition comprises one or more jojoba extracts. By "jojoba extract," Applicant means one or more materials extracted from any portion of the jojoba plant, including without limitation jojoba seed, pressed jojoba seed, jojoba roots, jojoba bark, jojoba leaves, and combinations thereof, and the like. Jojoba oil alone does not comprise a jojoba extract for the purpose of this Application. In certain embodiments, Applicant's composition comprises one or more jojoba extracts in combination with jojoba oil. Applicant's composition includes Simmondsin and/or Simmondsin derivatives. In certain embodiments, Applicants' composition further includes one or more jojoba proteins in combination with one or more jojoba peptide fragments. Applicant's invention further includes a method to whiten and exfoliate skin, comprising the step of topically administering to an individual a composition comprising one or more jojoba extracts in combination with one or more hydroxy acids.

BRIEF DESCRIPTION OF THE DRAWINGS

The invention will be better understood from a reading of the following detailed description taken in conjunction with the drawings in which like reference designators are used to designate like elements, and in which.

DETAILED DESCRIPTION OF THE PREFERRED EMBODIMENTS

The invention will be described as embodied in composition which includes one or more jojoba extracts in combination with one or more acids. By "jojoba extract," Applicant means one or more materials extracted from one or more parts of the jojoba plant, including but not limited to jojoba seed, pressed jojoba seed, jojoba roots, jojoba bark, jojoba leaves, and combinations thereof. Jojoba oil alone is not included within Applicant's definition of jojoba extract. In certain embodiments, Applicant's composition may include jojoba oil in combination with one or more jojoba extracts. Applicant's invention further includes use of Applicant's composition to affect the visual appearance of skin.

All patents, applications, test methods and publications referenced in this specification are hereby incorporated by reference in their entirety. In case of conflict, the present description, including definitions, will prevail. The present invention is directed in part to a composition which is useful as a skin whitening and skin exfoliation agent. Specifically, the invention is directed in part to a composition comprising one or more extracts from one or more jojoba plant parts in combination with one or more acidic compounds. In certain embodiments, Applicant's composition comprises Simmondsin and/or Simmondsin derivatives.

TABLE I recites the reported weight percents of Simmondsin/Simmondsin derivatives and jojoba oil in various jojoba plant parts.

TABLE I

| PLANT PART | WEIGHT PERCENT SIMMONDSIN | WEIGHT PERCENT JOJOBA OIL |
|---|---|---|
| Core wood | 0.45 | — |
| Leaves | 0.19 | 2.0 |
| Twigs | 0.63 | 1.1 |

Jaime Wisniak, The Chemistry and Technology of Jojoba Oil, America Oil Chemists' Society, at page 223.

In certain embodiments, Applicant's composition comprises a one or more proteins which naturally occur in the jojoba plant and/or or a plurality of peptide fragments and/or a plurality of amino acids. For example, jojoba seed comprises about 15 weight percent protein material. By "peptide fragments," Applicant means one or more amino acid oligomers derived from the cleavage of one or more jojoba proteins.

Figure 1:
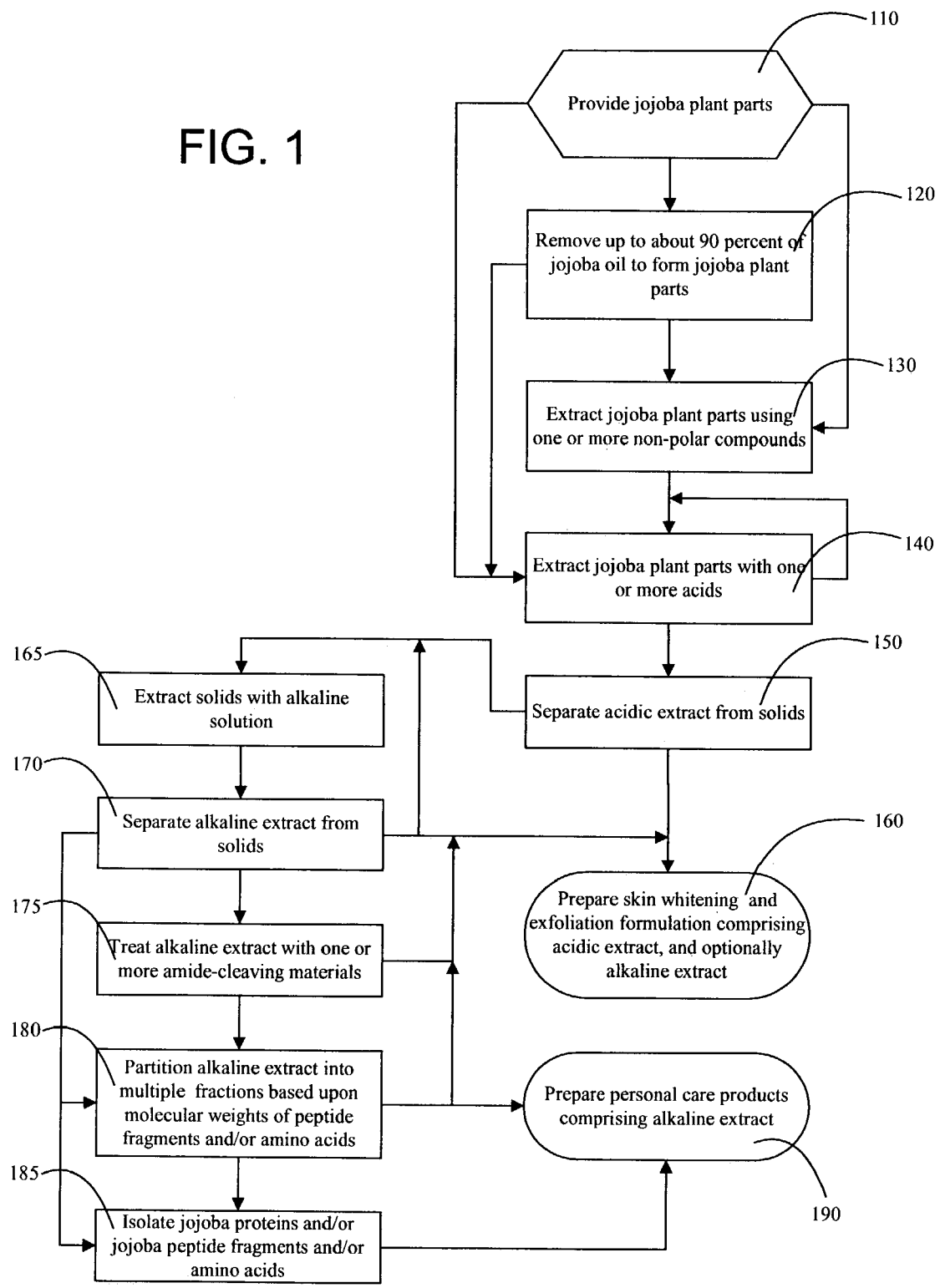
FIGS. 1 and 2 are flow charts summarizing the steps of Applicant's method to form his composition.

FIG. 1 summarizes Applicant's method to prepare his composition. Referring now to FIG. 1, in step 110 Applicant's method provides one or more parts of the jojoba plant. Such jojoba plant parts include, without limitation, seed, pressed seed, hulls, bark, roots, leaves, stems, and the like, but not jojoba oil alone. In certain embodiments, step 110 includes providing jojoba seed. In certain embodiments, jojoba seed is provided by the Desert Whale Jojoba Company of Tucson, Ariz. Jojoba seed comprises approximately 50 percent jojoba oil. The various parts of the jojoba plant, including jojoba seed, further comprises a complex mixture of jojoba oil, jojoba proteins, carbohydrates, Simmondsin, Simmondsin derivatives, and other phytochemicals. In certain embodiments, Applicant's method transitions from step 110 to step 120. In certain embodiments, Applicants' method transitions from step 110 to step 130. In certain embodiments, Applicant's method transitions from step 110 to step 140.

In step 120, Applicant's method removes up to about 90 percent of the jojoba oil disposed in the plant parts of step 110. In certain embodiments, step 120 comprises mechanically pressing the jojoba plant parts of step 110. In certain embodiments, such mechanical pressing is performed using an expeller apparatus. The solid material remaining after removal of jojoba oil from jojoba plant parts is sometimes referred to as "jojoba meal." This jojoba meal comprises up to about 12 percent residual jojoba oil in addition to a complex mixture of jojoba proteins, sugars, Simmondsin, and other phytochemicals. In certain embodiments, Applicant's method transitions from step 120 to step 130. In certain embodiments, Applicant's method transitions from step 120 to step 140.

As noted above, the various parts of the jojoba plant include a variety of jojoba proteins and amino acids. Table I recites the amino-acid composition of the jojoba meal of step 120.

TABLE I

| AMINO ACID | WEIGHT PERCENT |
|---|---|
| Lysine | 1.45 |
| Histidine | 0.61 |
| Arginine | 1.95 |
| Aspartic Acid | 2.82 |
| Threonine | 1.41 |
| Serine | 1.53 |
| Glutamic Acid | 3.36 |
| Proline | 1.44 |
| Glycine | 2.45 |
| Alanine | 1.19 |
| Valine | 1.54 |
| Methionine | 0.35 |
| Isoleucine | 1.03 |
| Leucine | 2.02 |
| Tyrosine | 1.07 |
| Phenylalanine | 1.23 |
| Cystine | 0.8 |
| Tryptophan | 0.32 |
| TOTAL | 26.57 |

In step 130, the jojoba plant parts of step 110/120 are extracted using one or more non-polar compounds. By a non-polar compound, Applicant means a material having a dielectric constant of about 2 or less. Such non-polar compounds include, without limitation, pentane, hexane, cyclohexane, and the like.

In certain embodiments, step 130 further includes using super critical $CO_2$ to extract the jojoba meal. Super critical carbon dioxide comprises highly pressurized carbon dioxide. At pressures of 250 to 350 times atmospheric pressure, $CO_2$ takes on the density of a liquid and the viscosity of a gas, making it an efficient solvent. In its pressurized state, $CO_2$ is pumped into a sealed chamber containing jojoba meal, where it is allowed to circulate to remove the residual jojoba oil. Two of the major advantages of $CO_2$ are that it does not leave a chemical residue and it has a minimal to no effect on the structure of the extracted jojoba oil. In certain embodiments, step 130 includes extracting the pressed jojoba plant parts with one or more solvents having a dielectric constant of about 6 or less. Such solvents include, without limitation, methyl formate, methyl acetate, ethyl acetate, ethers, and halogenated alkyls.

In step 140, the one or more jojoba plant parts are extracted with one or more acids. In certain embodiments, step 140 includes milling the jojoba meal to a powder. In certain embodiments, the milled jojoba meal has a average particle size of 50 microns with a standard deviation of 1.83. In certain embodiments, the milled jojoba meal has no particles larger than about 180 microns.

In certain embodiments, step 140 includes extracting the one or more jojoba plant parts with one or more acids in combination with one or more alcohols and/or one or more diols and/or one or more polyols. In certain embodiments, the one or more acids of step 140 include, for example, formic acid, acetic acid, propionic acid, and the like. In certain embodiments, the one or more acids of step 140 comprise one or more hydroxy-acids. By "hydroxy-acid," Applicant means a compound having a carboxylic acid functionality and a hydroxy functionality. In certain embodiments, the one or more hydroxy-acids of step 140 include one or more alpha-hydroxy acids. Such alpha-hydroxy acids include, without limitation, glycolic acid, lactic acid, mandelic acid, malic acid, citric acid, tartaric acid, and combinations thereof. In certain embodiments, the one or more acids of step 140 include one or more beta-hydroxy acids, such as and without limitation, salicylic acid, beta hydroxybutanoic acid, tropic acid, trethocanic acid, and the like, and mixtures thereof. In certain embodiments, the one or more acids of step 140 include one or more alpha hydroxy acids in combination with one or more beta-hydroxy acids.

In certain embodiments, step 140 includes maintaining the pH of the extract at about 3 by small incremental additions of acid. In certain embodiments, step 140 includes maintaining the pH of the extract at about 4 by small incremental additions of acid. In certain embodiments, step 140 includes maintaining the pH of the extract at about 4.5 by small incremental additions of acid.

In certain embodiments the one or more alcohols include, for example, butanol, pentanol, hexanol, and the like. In certain embodiments, the one or more diols include, for example, propylene glycol, polyethylene oxide diol, polypropylene oxide diol, and the like. In certain embodiments, the one or more polyols include, for example, glycerin, carbohydrate acetates, and the like.

Applicant has found that extraction of jojoba plant parts with one or more acids in combination with one or more alcohols/diols/polyols extracts, inter alia, Simmondsin and/ or Simmondsin derivatives. A substantial amount of the plurality of jojoba proteins, however, remain in the jojoba plant part, i.e. in the solid materials rather than being removed in the extract.

By "Simmondsin," Applicant means Compound I wherein R2 is hydrogen, R3 is OH, R4 is OCH₃ and R5 is OCH₃. By "Simmondsin derivative," Applicant means Compound I wherein R2 is other than hydrogen, R3 is other than OH, R4 is other than OCH₃, and R5 is other than OCH₃.

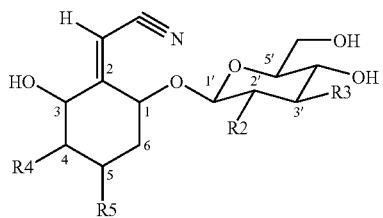

I

In certain embodiments, the R2 moiety of Compound I comprises a Ferulic acid moiety comprising compound II.

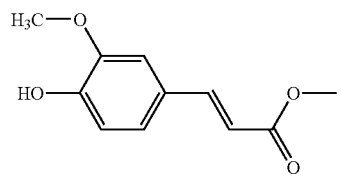

II

TABLE I summarizes Simmondsin and/or Simmondsin derivatives that comprise various embodiments of Applicant's composition.

TABLE I

| Compound | R2 | R3 | R4 | R5 | Name |
|---|---|---|---|---|---|
| III | H | OH | OCH₃ | OCH₃ | Simmondsin |
| IV | H | OH | OH | OCH₃ | 4-Demethylsimmondsin |
| V | H | OH | OCH₃ | H | 5-Demethylsimmondsin |
| VI | H | OH | OH | OH | Didemethylsimmondsin |
| VII | Compound II | OH | OCH₃ | OCH₃ | Simmondsin 2'-trans-ferulate |
| VIII | OH | Compound II | OCH₃ | OCH₃ | Simmondsin 3'-trans-ferulate |
| IX | Compound II | OH | OH | OCH₃ | 4-Demethylsimmondsin 2'-trans-ferulate |
| X | Compound II | OH | OCH₃ | OH | 5-Demethylsimmondsin 2'-trans-ferulate |
| XI | Compound II | OH | OH | OH | Didemethylsimmondsin trans-ferulate |

In step 150, Applicant's method separates the solids comprising one or more jojoba plant parts from the acidic extract formed in step 140. In certain embodiments, step 150 includes separating the solids from the extract by filtration. In certain embodiments, step 150 includes separating the solids from the extract by centrifugation. In certain embodiments, step 150 includes decanting the liquid extract from the remaining jojoba plant parts.

In certain embodiments, the extraction of step 140 is performed multiple times. In certain embodiments, the jojoba plant parts are extracted once. In certain embodiments, the jojoba plant parts are extracted twice. In certain embodiments, the jojoba plant parts are extracted three times. In certain embodiments, the jojoba plant parts are extracted more than three times. In the multiple extraction embodiments, the solid material separated in step 150 is again extracted according the step 140. In these embodiments, the multiple acidic extracts formed in step 140, and isolated in step 150, are combined.

In step 160, the acidic extract separated in step 150 is used to formulate one embodiment of Applicant's skin whitening/skin exfoliation composition. The acidic extract formed in step 140, and separated in step 150, comprises one or more hydroxy-acids in combination with a plurality of jojoba extracts. Such jojoba extracts comprise tyrosinase inhibitors, and/or melanin cell synthesis inhibitors. After topical application, such tyrosinase inhibition and/or melanin cell synthesis inhibition, results in skin whitening. Topical application of one or more alpha-hydroxy acids, and/or one or more beta-hydroxy acids, promotes dissolution of adhesions between cells in the upper layers of the skin. Such topical application of one or more hydroxy acids results in shedding dry scales from the skin, i.e. exfoliation. Such exfoliation stimulates the growth of new skin thereby providing a rejuvenated, fresher complexion.

In certain embodiments, Applicant's composition of step 160 further includes a cosmetically acceptable carrier and/or a pharmaceutically acceptable carrier. By "cosmetically acceptable" and "pharmaceutically acceptable," Applicant means those drugs, medicaments, or inert ingredients which are suitable for use in contact with the tissues of humans and lower animals without undue toxicity, incompatibility, instability, irritation, and the like, commensurate with a reasonable benefit/risk ratio. In certain embodiments, the cosmetically acceptable vehicle will form from about 1 weight percent to about 99.9 weight percent of Applicant's composition. In certain embodiments, the cosmetically acceptable vehicle comprises between about 50 weight percent and about 99 weight percent of Applicant's composition. In certain embodiments, Applicant's composition comprises a cream, an ointment, a foam, a lotion, a plaster, or an emulsion.

In certain embodiments, the Applicant's composition of step 160 has a pH of about 3. In certain embodiments, the Applicant's composition has a pH of about 4. In certain embodiments, the Applicant's composition has a pH of about 5. In certain embodiments, the Applicant's composition has a pH of about 6. In certain embodiments, the Applicant's composition has a pH of about 7. In certain embodiments, the Applicant's composition has a pH between 7 and 8.

Example I is presented to further illustrate to persons skilled in the art how to make and use the invention and to identify certain embodiments thereof. This example is not intended as a limitation, however, upon the scope of the invention, which is defined only by the appended claims.

TABLE II

| COMPONENT | WEIGHT PERCENT |
| --- | --- |
| Deionized Water | 36.8 |
| Jojoba Plant Parts | 25 |

TABLE III

| COMPONENT | WEIGHT PERCENT |
| --- | --- |
| Deionized Water | 8 |
| Glycolic Acid (70%) | 4 |
| Lactic Acid (88%) | 1.2 |
| Glycerin | 8 |
| Propylene Glycol | 4 |

TABLE IV

| COMPONENT | WEIGHT PERCENT |
| --- | --- |
| Sodium Hydroxide (50%) | 2.8 |
| Transcutol CG | 8 |
| Guar Hydroxypropyltrimonium Chloride | 1 |
| Phenobact | 1 |
| Fragrance | 0.2 |

The components of TABLE II are mixed in a first vessel equipped with side scraping by first adding the water and then the jojoba meal. That mixture is stirred until uniform.

In a second vessel, the glycolic acid, lactic acid, glycerin, and propylene glycol, are added to the water component with stirring The mixture of Table III is added to the first vessel with mixing. After the addition is complete, the mixture is heated to about 75° C. to about 80° C. with mixing for about ten minutes. After holding the mixture at between about 75° C. and about 80° C. for about ten minutes, the mixture is cooled to between about 45° C. and about 50° C. and filtered.

The acidic filtrate is returned to the second vessel. Thereafter, the sodium hydroxide of Table III is slowly added. The remaining components of TABLE IV are mixed in a third vessel until uniform. That uniform mixture is then added to the heated, and stirred mixture in the second vessel to prepare this embodiment of Applicants' composition. This embodiment of Applicant's composition was mixed until uniform and then cooled. The pH of this embodiment of Applicant's composition is between about 4 and about 4.5.

In step 165, Applicant's method extracts the solids isolated in step 150 with an alkaline solution. In certain embodiments, step 165 includes treating the solids of step 150 with an aqueous alkaline solution at pH 10 using a weight to volume ratio of about 1:15 with respect to the solids and the alkaline solution. In certain embodiments, the alkaline solution of step 165 comprises a sodium hydroxide solution. In certain embodiments, the alkaline solution of step 165 comprises a potassium hydroxide solution.

Example II is presented to further illustrate to persons skilled in the art how to make and use the invention and to identify certain embodiments thereof. This example is not intended as a limitation, however, upon the scope of the invention, which is defined only by the appended claims.

EXAMPLE II

Two hundred grams of solids isolated in step 150 are slurried in about 3 liters of a sodium hydroxide solution having a pH of about 10 for about thirty minutes with stirring at room temperature. The pH is maintained at about 10 by adding 0.1N NaOH solution.

In step 170, the alkaline extract is separated from the remaining solid materials. In certain embodiments, step 170 includes separating the solids from the extract by filtration. In certain embodiments, step 170 includes separating the solids from the extract by centrifugation. In certain embodiments, step 170 includes decanting the liquid extract from the remaining jojoba plant parts.

In certain embodiments, the extraction of step 160 is performed multiple times. In certain embodiments, the jojoba plant parts are extracted once with an alkaline solution. In certain embodiments, the jojoba plant parts are extracted twice with an alkaline solution. In certain embodiments, the jojoba plant parts are extracted three times with an alkaline solution. In certain embodiments, the jojoba plant parts are extracted more than three times with an alkaline solution. In the multiple extraction embodiments, the solid material separated in step 170 is again extracted according the step 160. In these embodiments, the multiple alkaline extracts formed in step 160, and isolated in step 170, are combined.

In certain embodiments, Applicant's method transitions from step 170 to step 160. In certain embodiments, Applicant's method transitions from step 170 to step 175. In certain embodiments, Applicant's method transitions from step 170 to step 180. In certain embodiments, Applicant's method transitions from step 170 to step 185.

In certain embodiments, Applicant's method transitions from step 170 to step 160 wherein the alkaline extract isolated in step 170 is used to formulate Applicants' skin whitening/exfoliation composition of step 160. In these embodiments, the alkaline extract of step 170 is substituted for the NaOH component of Table IV with the volume of alkaline extract of step 170 used being adjusted to keep the pH of the final composition to be between about 4 and about 4.5.

In step 175, the extract of step 170 is treated with one or more compounds to effect cleavage of one or more amide bonds in one or more jojoba proteins. In certain embodiments, step 175 includes using one or more protease enzymes. In certain embodiments, step 175 includes using one or more acids, such as hydrochloric acid. In certain embodiments, Applicants' method transitions from step 175 to step 160 wherein Applicant's method forms a skin whitening/skin exfoliation composition comprising one or more jojoba proteins and/or one or more peptide fragments formed from one or more jojoba proteins and/or one or more amino acids formed from one or more jojoba proteins. In certain embodiments, Applicant's method transitions from step 175 to step 180.

In step 180, the treated extract of step 175 is partitioned into multiple fractions, where each of those fractions comprises a different molecular weight distribution of amino acids, and/or peptide fragments, and/or jojoba proteins. In certain embodiments, the one or more fractions of step 180 further include one or more carbohydrate compounds. In certain embodiments, Applicant's method transitions from step 180 to step 160. In certain embodiments, Applicant's method transitions from step 180 to step 185 wherein one or more jojoba proteins and/or one or more jojoba peptide fragments are isolated.

In certain embodiments, step 185 comprises precipitating the extract of step 170 or step 180 with 0.5N hydrochloric acid at a pH of about 4. In certain embodiments, step 185 further includes filtering the precipitated proteins/peptide fragments and washing those proteins/peptide fragments with water. In certain embodiments, the isolated proteins/peptide fragments of step 185 are filtered and then freeze-dried. In certain embodiments, step 185 includes treating the extract of step 170/180 with activated carbon to decolorize the protein/peptide solution prior to precipitation of the proteins/peptide fragments.

In certain embodiments, Applicant's method transitions from step 180/step 185 to step 190 wherein Applicant's method formulates personal care products. Such personal care products include, without limitation, skin exfoliation products, skin moisturizers, massage oils, soaps, sunscreens, skin cleaners, and the like.

In certain embodiments, Applicant's composition of step 190 further includes a cosmetically acceptable carrier and/or a pharmaceutically acceptable carrier. By "cosmetically acceptable" and "pharmaceutically acceptable," Applicant means those drugs, medicaments, or inert ingredients which are suitable for use in contact with the tissues of humans and lower animals without undue toxicity, incompatibility, instability, irritation, and the like, commensurate with a reasonable benefit/risk ratio. In certain embodiments, the cosmetically acceptable vehicle will form from about 1 weight percent to about 99.9 weight percent of Applicant's composition. In certain embodiments, the cosmetically acceptable vehicle comprises between about 50 weight percent and about 99 weight percent of Applicant's composition. In certain embodiments, Applicant's composition comprises a cream, an ointment, a foam, a lotion, a plaster, or an emulsion.

In certain embodiments, Applicant's composition of step 160, formed using steps 110, 120, 130, 140, 150, comprises less than about one percent proteins, peptide fragments, and amino acids. In certain embodiments, Applicant's composition of step 160, formed using steps 110, 120, 130, 140, 150, and 165, includes up to about 25 weight percent of jojoba proteins. In certain of these embodiments, the composition of step 160 comprises one or more jojoba proteins having a molecular weight greater than about 100,000 Daltons. In certain of these embodiments, the composition of step 160 comprises one or more jojoba proteins having a molecular weight greater than about 50,000 Daltons.

In certain embodiments, Applicant's composition of step 160, formed using steps 110, 120, 130, 140, 150, 165, and 175, includes up to about 25 weight percent of a plurality of amino acids an/or a plurality of peptide fragments. In certain of these embodiments, the composition of step 160 comprises one or more peptide fragments having a molecular weight greater than about 10,000 Daltons.

In certain embodiments, Applicant's personal care formulations of step 190, formed using steps 110, 120, 130, 140, 150, 165, 170, and optionally step 180, and optionally step 185, comprise one or more jojoba proteins having a molecular weight greater than about 100,000 Daltons. In certain embodiments, Applicant's personal care formulations of step 190, formed using steps 110, 120, 130, 140, 150, 165, 170, and optionally step 180, and optionally step 185, comprise one or more jojoba proteins having a molecular weight greater than about 50,000 Daltons. In certain embodiments, Applicant's personal care formulations of step 190, formed using steps 110, 120, 130, 140, 150, 165, 170, 175, and optionally 180, and optionally step 185, comprise one or more jojoba peptide fragments having a molecular weight greater than about 10,000 Daltons.

The embodiments of Applicants' method recited in FIG. 1 may be implemented separately. Moreover, in certain embodiments, individual steps recited in FIG. 1 may be combined, eliminated, or reordered. For example, certain embodiments of Applicant's method include steps 110, 140, 150, and 160. Other embodiments of Applicant's method include steps 110, 120, 140, 150, and 160. Other embodiments of Applicant's method include steps 110, 130, 140, 150, and 160. Other embodiments of Applicant's method include steps 110, 120, 130, 140, 150, and 160.

Other embodiments of Applicant's method includes steps 110, 140, 150, 160, 165, and 170. Other embodiments of Applicant's method includes steps 110, 120, 140, 150, 160, 165, and 170. Other embodiments of Applicant's method includes steps 110, 130, 140, 150, 160, 165, and 170. Other embodiments of Applicant's method includes steps 110, 120, 130, 140, 150, 160, 165, and 170.

Other embodiments of Applicant's method includes steps 110, 140, 150, 165, 170, 180, and 190. Other embodiments of Applicant's method includes steps 110, 120, 140, 150, 165, 170, 180, and 190. Other embodiments of Applicant's method includes steps 110, 120, 130, 140, 150, 165, 170, 180, and 190. Other embodiments of Applicant's method includes steps 110, 130, 140, 150, 165, 170, 180, and 190.

Other embodiments of Applicant's method includes steps 110, 140, 150, 165, 170, 180, 185, and 190. Other embodiments of Applicant's method includes steps 110, 120, 140, 150, 165, 170, 180, 185, and 190. Other embodiments of Applicant's method includes steps 110, 120, 130, 140, 150, 165, 170, 180, 185, and 190. Other embodiments of Applicant's method includes steps 110, 130, 140, 150, 165, 170, 180, 185, and 190.

Figure 2:
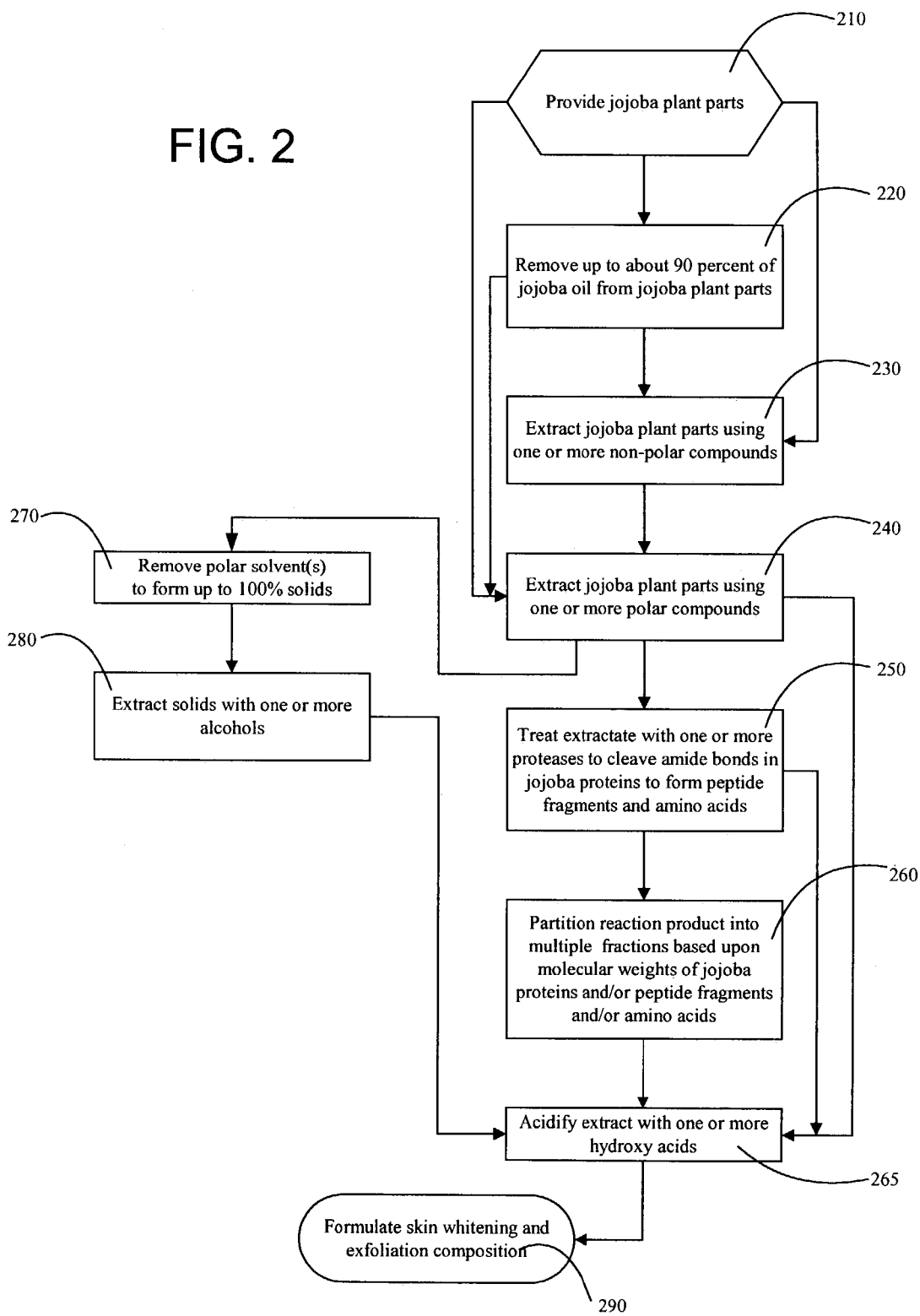

FIG. 2 summarizes the steps in a second embodiment of Applicant's method to prepare Applicant's skin whitening/skin exfoliating formulation. Referring now to FIG. 2, steps 210, 220, and 230, parallel steps 110, 120, and 130, discussed above.

In step 240, the jojoba plant parts are extracted with one or more polar compounds. By polar compound, Applicant means a material having a dielectric constant of about 10 or more. Such compounds include, without limitation, water, organic acids, salts of organic acids, inorganic acids, salts of inorganic acids, organic bases, salts of organic bases, inorganic bases, salts of inorganic bases, linear and cyclic alcohols, linear and cyclic ketones, dimethylsulfoxide, dimethylsulfone, and the like. In certain embodiments, step 240 further includes milling the jojoba meal to a powder.

In certain embodiments, Applicant's method transitions from step 240 to step 250. In certain embodiments, Applicant's method transitions from step 240 to step 265. In certain embodiments, Applicant's method transitions from step 240 to step 270.

In step 250, the polar solvent extract of step 240 is treated with one or more compounds to effect cleavage of one or more amide bonds in one or more jojoba-derived proteins. In certain embodiments, step 250 includes using one or more protease enzymes. In certain embodiments, step 250 includes using one or more acids, such as hydrochloric acid.

In step 260, the product of step 250 is partitioned into multiple fractions, where each of those fractions comprises a different molecular weight distribution of amino acids, and/or peptide fragments, and/or jojoba proteins. In certain embodiments, the one or more fractions of step 260 further include one or more carbohydrate compounds. In certain embodiments, the one or more fractions of step 260 further include Simmondsin and/or Simmondsin derivatives. In certain embodiments, the one or more fractions of step 260 further include jojoba oil. The jojoba oil component is added in step 260.

In step 265, the extract of step 240, or the separated fractions of step 260, or the extract of step 280, is acidified with one or more hydroxy acids to a pH between about 3 and about 4.5. By "hydroxy-acid," Applicant means a compound having a carboxylic acid functionality and a hydroxy functionality. In certain embodiments, the one or more hydroxy-acids of step 265 include one or more alpha-hydroxy acids. Such alpha-hydroxy acids include, without limitation, glycolic acid, lactic acid, mandelic acid, malic acid, citric acid, tartaric acid, and combinations thereof. In certain embodiments, the one or more acids of step 265 include one or more beta-hydroxy acids, such as and without limitation, salicylic acid, beta hydroxybutanoic acid, tropic acid, trethocanic acid, and the like, and mixtures thereof. In certain embodiments, the one or more acids of step 265 include one or more alpha hydroxy acids in combination with one or more beta-hydroxy acids.

In certain embodiments, step 265 includes lowering the pH of the extract to about 3. In certain embodiments, step 265 includes lowering the pH of the extract to about 4. Applicant's method transitions from step 265 to step 290.

In step 270, Applicant's method removes the one or more polar compounds from the extract of step 240 to form a material having up to 100 percent solids. Step 270 includes conventional methods and apparatus such as rotary evaporation, atmospheric evaporation, use of a fluidized bed, and the like. Applicant's method transitions from step 270 to step 280 wherein the high percentage solids material of step 270 is extracted with one or more alcoholic solvents. In certain embodiments, step 280 includes extracting the solids of step 270 with ethanol. Applicant's method transitions from step 280 to step 265.

In step 290, Applicant's method forms Applicant's skin whitening/skin exfoliation composition using the acidified extract of step 265. In certain embodiments, Applicant's composition of step 290 further includes a cosmetically acceptable carrier and/or a pharmaceutically acceptable carrier. By "cosmetically acceptable" and "pharmaceutically acceptable," Applicant means those drugs, medicaments, or inert ingredients which are suitable for use in contact with the tissues of humans and lower animals without undue toxicity, incompatibility, instability, irritation, and the like, commensurate with a reasonable benefit/risk ratio. In certain embodiments, the cosmetically acceptable vehicle will form from about 1 weight percent to about 99.9 weight percent of Applicant's composition. In certain embodiments, the cosmetically acceptable vehicle comprises between about 50 weight percent and about 99 weight percent of Applicant's composition. In certain embodiments, Applicant's composition comprises a cream, an ointment, a foam, a lotion, a plaster, or an emulsion.

Applicant's composition, formed using steps 210, 220, 230, 240, 265, 270, 280, and 290, is essentially free of proteins, peptide fragments, and amino acids. Applicant's composition, formed using steps 210, 220, 230, 240, 265, and 290 includes up to about 25 weight percent of jojoba proteins. Applicant's composition, formed using steps 210, 220, 230, 240, 250, optionally 260, 265, and 290, includes up to about 25 weight percent of a plurality of amino acids an/or a plurality of peptide fragments.

In certain embodiments, Applicant's skin whitening/skin exfoliation composition of step 160 includes jojoba oil. In embodiments of Applicant's method that include steps 120 and 130, the jojoba oil component is added in step 160. In certain embodiments, Applicant's personal care formulations of step 190 include jojoba oil. In embodiments of Applicant's method that include steps 120 and 130, the jojoba oil component is added in step 190. In certain embodiments, Applicant's skin whitening/skin exfoliation composition of step 290 includes jojoba oil. In embodiments of Applicant's method that include steps 220 and 230, the jojoba oil component is added in step 290.

Jojoba oil comprises a mixture of naturally-occurring compounds obtained from the jojoba seed, sometimes called the jojoba bean. Jojoba seed contains about 50 weight percent of a yellow oil commonly referred to as jojoba oil. In contrast to other vegetable oils which comprise a mixture of triglycerides, jojoba oil comprises a mixture of long-chain esters.

As those skilled in the art will appreciate, carboxylic ester XV can be formed by the reaction of alcohol XIV and carboxylic acid XIII. In addition, an ester-group-containing compound, such as many of the constituents of jojoba oil, can be described as comprising an R5 component and an R6 component.

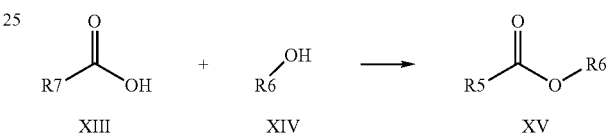

XIII   XIV   XV

Jojoba oil includes a variety of ester-group-containing compounds wherein the R7 component comprises a mixture of carbon-containing moieties having, primarily, 17, 18, 20, and 22 carbon atoms, and wherein the R6 component comprises a mixture of carbon-containing moieties having, primarily, 19, 20, 22, and 24 carbon atoms. Furthermore, it is known that the R7 component of these various jojoba oil ester-group-containing constituents includes at least one carbon-carbon double bond having a cis-configuration. Sometimes such a cis-configuration is known as the Z-configuration. It is further known that the R6 component of these various jojoba oil ester-group-containing constituents includes at least one carbon-carbon double bond having a cis-configuration. Sometimes such a cis-configuration is known as the Z-configuration.

By "jojoba oil," Applicant means naturally-occurring jojoba oil and/or one or more derivatives of naturally-occurring jojoba oil. Certain derivatives of jojoba oil are known in the art. For example, isomerization of the double bond in the R7 component, and/or the R6 component, of the various jojoba esters from the cis configuration to a trans configuration yields a material that is solid at room temperature, where that solid material includes one or more crystalline compounds. U.S. Pat. No. 4,329,298 teaches a method to isomerize jojoba oil and is hereby incorporated herein by reference.

In addition, hydrogenation of the double bond in the R7 component, and/or hydrogenation of the double bond in the R6 component, of the jojoba oil ester yields a crystalline, wax-like material. Substantially fully hydrogenated jojoba oil is a solid with a melting point upwards of 70° C. As those skilled in the art will appreciate, the degree of hydrogenation can be measured using an Iodine Value ("IV"). Naturally-occurring jojoba oil has an IV of between about 80 and 85. As the percentage of carbon-carbon double bonds hydrogenated increases, the IV of that hydrogenated material decreases. As the percentage of carbon-carbon double bonds hydrogenated increases, the degree of crystallinity and the melting point of that hydrogenated material also increase.

In certain embodiments, Applicant's skin whitening/exfoliation composition includes Lysine at a weight percent between about 0.01 and about 1, Histidine at a weight percent between about 0.01 and about 0.3, Arginine at a weight percent between about 0.01 and about 1, Aspartic Acid at a weight percent between about 0.05 and about 1.50, Threonine at a weight percent between about 0.01 and about 0.75, Serine at a weight percent between about 0.01 and about 0.8, Glutamic Acid at a weight percent between about 0.10 and about 1.75, Proline at a weight percent between about 0.01 and about 0.75, Glycine at a weight percent between about 0.05 and about 1.25, Alanine at a weight percent between about 0.05 and about 0.60, Valine at a weight percent between about 0.01 and about 0.77, Methionine at a weight percent between about 0.01 and about 0.25, Isoleucine at a weight percent between about 0.01 and about 0.54, Leucine at a weight percent between about 0.05 and about 1, Tyrosine at a weight percent between about 0.01 and about 0.53, Phenylalanine at a weight percent between about 0.05 and about 0.62, Cystine at a weight percent between about 0.01 and about 0.40, Tryptophan at a weight percent between about 0.01 and about 0.16, Simmondsin at a weight percent between about 0.01 and about 5, Fructose at a weight percent between about 0.01 and about 5, Glucose at a weight percent between about 0.01 and about 5, Sucrose at a weight percent between about 0.01 and about 1, and water at a weight percent between about 30 and about 98.

While the preferred embodiments of the present invention have been illustrated in detail, it should be apparent that modifications and adaptations to those embodiments may occur to one skilled in the art without departing from the scope of the present invention as set forth in the following claims.

I claim:

1. A composition which is effective as a skin whitening and skin exfoliation agent, said composition being formed by the steps of:
   (a) forming an aqueous mixture comprising jojoba meal;
   (b) adding one or more hydroxy acids to the mixture of part (a);
   (c) filtering the aqueous mixture of part (b) to form a filtrate;
   (d) adjusting the pH of the filtrate of part (c) to between about 4 and about 4.5.

2. The composition of claim 1, wherein said one or more hydroxy acids comprise one or more alpha-hydroxy acids.

3. The composition of claim 1, wherein said one or more hydroxy acids are selected from the group consisting of one or more alpha-hydroxy acids, one or more beta-hydroxy acids, and combinations thereof.

4. The composition of claim 1, further comprising Simmondsin.

5. The composition of claim 4, further comprising one or more jojoba proteins.

6. The composition of claim 4, further comprising one or more jojoba peptide fragments.

7. The composition of claim 4, further comprising one or more Simmondsin derivatives selected from the group consisting of 4-Demethylsimmondsin, 5-Demethylsimmondsin, Didemethylsimmondsin, Simmondsin 2'-trans-ferulate, Simmondsin 3'-trans-ferulate, 4-Demethylsimmondsin 2'-trans-ferulate, 5-Demethylsimmondsin 2'-trans-ferulate, Didemethylsimmondsin trans-ferulate, and mixtures thereof.

8. The composition of claim 1, further comprising a Ferulic acid moiety.

9. The composition of claim 1, further comprising:
   Lysine at a weight percent between about 0.01 and about 1;
   Histidine at a weight percent between about 0.01 and about 0.3;
   Arginine at a weight percent between about 0.01 and about 1;
   Aspartic Acid at a weight percent between about 0.05 and about 1.50;
   Threonine at a weight percent between about 0.01 and about 0.75;
   Serine at a weight percent between about 0.01 and about 0.8;
   Glutamic Acid at a weight percent between about 0.10 and about 1.75;
   Proline at a weight percent between about 0.01 and about 0.75;
   Glycine at a weight percent between about 0.05 and about 1.25, Alanine at a weight percent between about 0.05 and about 0.60;
   Valine at a weight percent between about 0.01 and about 0.77, Methionine at a weight percent between about 0.01 and about 0.25;
   Isoleucine at a weight percent between about 0.01 and about 0.54;
   Leucine at a weight percent between about 0.05 and about 1;
   Tyrosine at a weight percent between about 0.01 and about 0.53;
   Phenylalanine at a weight percent between about 0.05 and about 0.62;
   Cystine at a weight percent between about 0.01 and about 0.40;
   Tryptophan at a weight percent between about 0.01 and about 0.16;
   Simmondsin at a weight percent between about 0.01 and about 5;
   Fructose at a weight percent between about 0.01 and about 5;
   Glucose at a weight percent between about 0.01 and about 5;
   Sucrose at a weight percent between about 0.01 and about 1; and
   water at a weight percent between about 30 and about 98.

10. A method of promoting skin whitening and exfoliation, comprising the step of topically administering to an individual a composition in an amount effective to whiten and exfoliate skin, wherein said composition is formed by the steps of:
    (a) forming an aqueous mixture comprising jojoba meal;
    (b) adding one or more hydroxy acids to the mixture of part (a);
    (c) filtering the aqueous mixture of part (b) to form a filtrate;
    (d) adjusting the pH of the filtrate of part (c) to between about 4 and about 4.5.

11. The method of claim 10, wherein said composition comprises the composition of claim 4.

12. The method of claim 11, further comprising repeating the topical administration of said composition as required for effectiveness.

* * * * *